Figure 1:
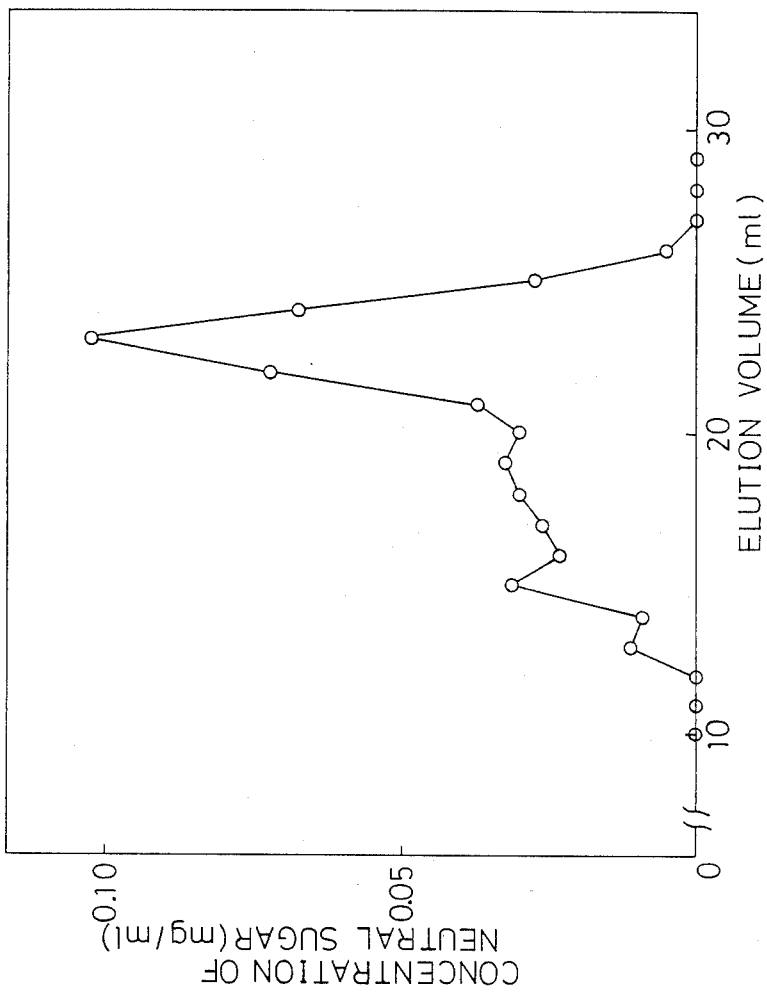

United States Patent [19]

Nakaya et al.

[11] Patent Number: 4,797,389
[45] Date of Patent: Jan. 10, 1989

[54] SUBSTANCE HAVING AN ANTI-INFECTIVE ACTIVITY

[75] Inventors: Rintaro Nakaya; Noboru Okamura, both of Tokyo; Takuji Kawashima, Kawasaki; Minoru Saito, Komae; Nabuya Yanai, Nakano; Tomohiro Toida, Hachioji; Hajime Yokota, Tokyo, all of Japan

[73] Assignee: Morinaga Milk Industry Co., Ltd., Tokyo, Japan

[21] Appl. No.: 861,771

[22] Filed: May 9, 1986

[30] Foreign Application Priority Data

May 9, 1985 [JP] Japan .................................. 60-96725

[51] Int. Cl.$^4$ ........................................... A61K 31/715
[52] U.S. Cl. ...................................... 514/54; 536/1.1
[58] Field of Search ........................... 514/54; 536/1.1

[56] References Cited

U.S. PATENT DOCUMENTS 4,210,641 7/1980 Brossard et al. ..................... 514/54

Primary Examiner—John W. Rollins
Attorney, Agent, or Firm—Sughrue, Mion, Zinn, Macpeak & Seas

[57] ABSTRACT

This invention relates to a substance having an anti-infective activity which comprises a polysaccharide separated from the cell wall of bacteria belonging to genus Bifidobacterium specified by *Bifidobacterium infantis*, *Bifidobacterium longum* and the mixture thereof, and mainly composed of glucose and galactose at the molar ratio of 1:about 2.8.

12 Claims, 2 Drawing Sheets

SUBSTANCE HAVING AN ANTI-INFECTIVE ACTIVITY

This invention relates to substance having an anti-infective activity (hereinafter referred to as "anti-infective substance") comprising a polysaccharide separated from the cell wall of bacteria belonging to genus Bifidobacterium (hereinafter referred to as "the bifidobacteria")

BACKGROUND OF THE ART AND PRIOR ART

The bifidobacteria are obligatory anaerobic, gram-positive bacilli always present in human intestine, and are known as useful bacteria which amount to 90% or more of intestinal microflora particularly in infants. Research on the interaction between enteric bacteria and a human being, a host, from the viewpoint of two aspects, i.e., harmfulness and usefulness is rapidly proceeding. The bifidobacteria which are main bacteria of intestinal microflora are known as bacteria having an inhibitory activity on colonization of harmful bacteria such as pathogenic bacteria in intestine, a suppressive activity on abnormal proliferation thereof in intestine, and a preventive activity on intoxication, intestinal infection and the like caused by harmful bacteria. Particularly in the case of babies whose immunity has not yet been developed, their intestinal microflora is of important significance as a flora which imparts a power of resistance to infectious diseases, and it is considered that proxotion of formation of a healthy intestinal microflora by the bifidobacteria is an effective means for reducing the danger of intestinal infection in babies. Intestinal infections often caused in infants are roughly classified into toxin type diseases caused by toxins produced by pathogenic bacteria, and infection type diseases caused by direct contact of pathogenic bacteria with intestinal tissues or cells and their invasion thereupon. The intestinal bifidofacteria produces acetic acid and lactic acid which inhibit proliferation of these pathogenic bacteria or their toxin production, and has an activity of directly inhibiting proliferation of the pathogenic bacteria. Nakaya et al. have reported that the bifidobacteria have a preventive activity on intracellular infection with *Shigella flexneri* which has the properties of invading cultured human cells (The Journal of Pediatric Practice Vol.47, No.5 P.723-728 (1984)).

On the other hand, as to the cell wall of the bifidobacteria or its constituents, utilization thereof as antitumor agents or carcinostatic agents has heretofore been known (Japanese Patent Publication No. 42271/81 and Japanese Unexaxined Patent Application Publication Nos. 103194/81, 212122/82 and 118712/84), but the anti-infective activity of these substances has not yet been reported. Further, all of the active materials in these inventions are characterized by containing peptides or proteins.

In order to develop a drug capable of preventing intestinal infection and infection in eyelid or superior trachea mucosa which are caused in infants and aged men, the present inventors noted the inhibitory activity of viable cells of the bifidobacteria on invasion of *Shigella flexneri* upon cells and searched for the active material of the bifidobacteria. As a result, the present inventors have found that a polysaccharide which is a constituent of the cell wall of the bifidobacteria has an inhibitory activity on invasion of *Shigela flexneri* upon cells, and have accomplished this invention on the basis of this finding.

OBJECTS OF THE INVENTION AND SUMMARY OF THE INVENTION

An object of this invention is to provide an anti-infective substance free from harmful side effects. Another object of this invention is to provide an anti-infective substance which specifically acts only on pathogenic bacteria which invade cells.

This invention is an anti-infective substance comprising a polysaccharide separated from the cell wall of the bifidobacteria.

CONCRETE EXPLANATION OF THE INVENTION

The bacteria used for producing the anti-infective substance of this invention are well-known bifidobacteria described in "Bergey's manual of determinative bacteriology", edited by R. E. Buchanan & N. E. Gibbons 8th ed. p.669, The Williams & Wilkins Co., 1974, are listed in The American Type Culture Collection; Catalogue of Strains I, 11th ed. 1978 (a catalogue of ATCC), and are easily available.

The anti-infective substance of this invention is produced in the following manner. The bifidobacteria are anaerobically cultured by a conventional method and subjected to heat pasteurization at 60° to 65° C. for 30 to 60 minutes, and cells are collected by centrifugation. The cells are washed with distilled water or physiological saline and disrupted by a conventional method (for example, treatment by means of a ultrasonic cell disintegrator at 20 KHz to 40 KHz for 20 to 60 minutes), and the disrupted cells were collected by centrifugation at 20,000 to 30,000 x g for 30 to 60 minutes. Subsequently, the disrupted cells were treated with proteolytic enzymes and nucleases by a conventional method to hydrolyze proteins and nucleic acids contained in said disrupted cells, which are then removed to obtain a cell wall fraction. Said cell wall fraction was dialyzed against distilled water and freeze-dried. Said freeze-dried fraction was suspended in a weakly acidic aqueous solution (e.g., 0.1 N HCl or 5% trichloroacetic acid) of 100 to 250 times as much as the freeze-dried fraction, and the resulting suspension was maintained at 30° to 60° C. for 1 to 24 hours to be subjected to hydrolysis treatment, whereby a polysaccharide is separated from the cell wall. Next, the suspension is neutralized with 2N NaOH, and insoluble materials are separated by filtration, after which the filtrate is concentrated under reduced pressure, and alcohol is added thereto to a final concentration of 90% to precipitate said polysaccharide. The polysaccharide precipitate is recovered by centrifugation and dissolved in distilled water and if necessary, the precipitation in alcohol is repeated several times, whereby the polysaccharide is obtained in a pure form. Said polysaccharide is dialyzed against distilled water and freeze-dried, whereby the polysaccharide is obtained in the form of white, tastless and odorless powder. The polysaccharide thus produced has the following physicochemical properties. These physicochemical properties were investigated by using the polysaccharide obtained in Example 1.

(1) Molecular weight

The polysaccharide was applied to gel filtration chromatography on TSK G3000 SW column (mfd. by Toyo Soda Manufacturing Co., Ltd.) and the molecular weight distribution was determined by quantitatively analyzing the polysacchalide by a phenol-sulfuric acid method. The result was as shown in FIG. 1: a high peak was observed at a molecular weight of 18,000 dalton and the molecules were widely distributed in the molecular weight range of 15,000 to 200,000 dalton.

(2) Solubility

The polysaccharide was soluble in water but insoluble in organic solvents.

(3) Infrared absorption spectrum

Figure 2:
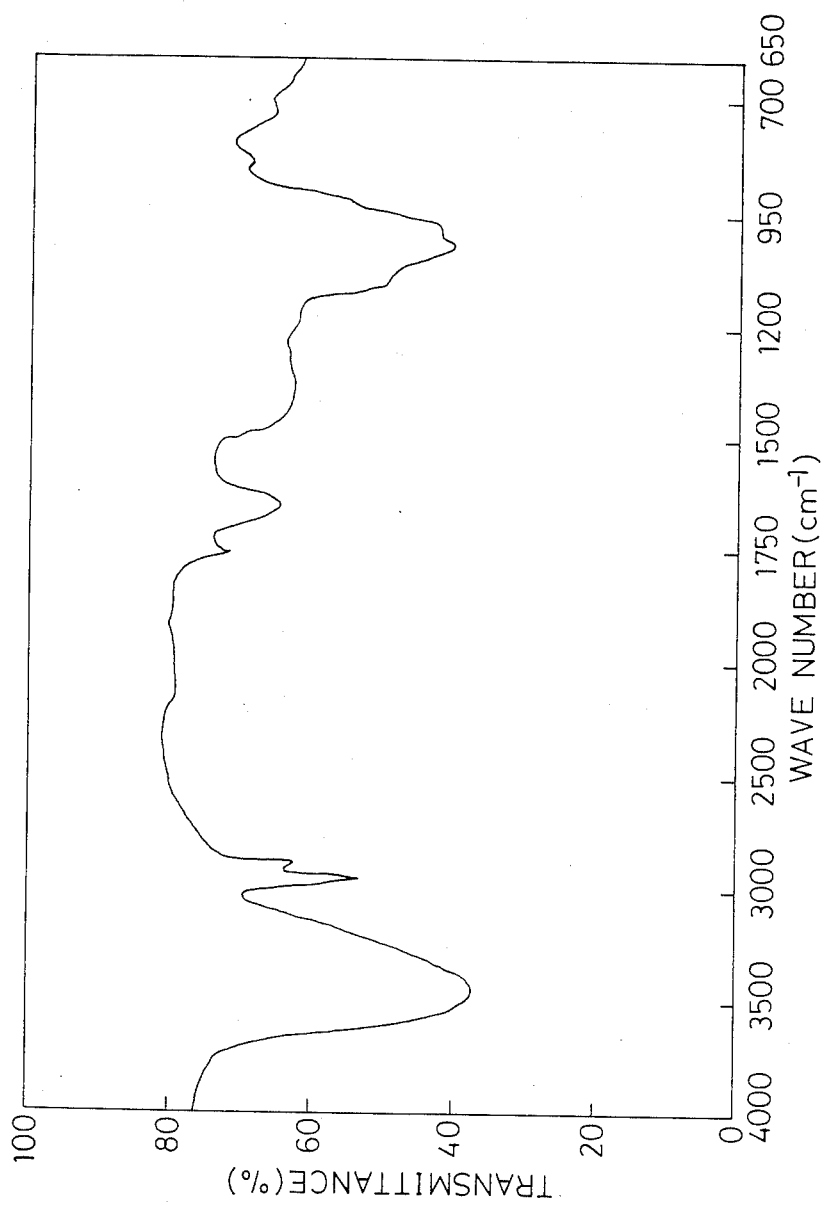

An infrared absorption spectrum was measured by the KBr tablet method. The result was as shown in FIG. 2: characteristic absorption were observed at 3600 to 3200 cm$^{-1}$ (strong), 1160 cm$^{-1}$ to 1000 cm$^{-1}$ (strong), 2950 to 2850 cm$^{-1}$ (medium) and 1640 cm$^{-1}$ (medium).

(4) Color reactions

The polysaccharide produced a color characteristic of sugar by α-naphthol-sulfuric acid reaction, indole-sulfuric acid reaction, anthrone-sulfuric acid reaction and phenol-sulfuric acid reaction. It did not produce a color characteristic reactions of protein or peptide by the biuret reaction and Lowry-Folin's reaction.

(5) Constituent saccharides

The polysaccharide was dissolved in 1N sulfuric acid, hydrolized at 100° C. for 6 hours, passes through a column packed with Amberlite IRA-400, dried under vacuum, converted to TMS derivatives, and then analyzed by gas chromatography. As a result, it was found that the polysaccharide were mainly composed of glucose and galactose, and that the molar ratio of glucose to galactose was 1:about 2.8.

(6) Elementary analysis

Results of elementary analysis by a conventional method are as follows: 44.6% of carbon, 6.2% of hydrogen and less than 0.2% of nitrogen.

(7) Color and other properties

The polysaccharide was white, tasteless and odorless.

From the above-mentioned physicochemical properties, it is apparent that the polysaccharide which is the anti-infective substance of this invention comprises substantially only glucose and galactose and contains neither protein nor peptide. The polysaccharide is used as an anti-infective agent for intestine by orally administering it as it is or after dilution with a suitable powdered excipient, or as an anti-infective agent for eyelid by direct adminisration to eyelid after dissolution in water or physiological saline.

This invention is further explained in more detail with reference to the following test examples.

TEST 1

Anti-infective Test in Cells

A method for infection experiments is in accordance with the method of Okamura et al. (Infection and Immunity, Vol. 39, P.505 to 513 (1983)).

Each of polysaccharides produced in the same manner as in Examples 1 and 2 was added in an amount of 2, 1.5, 1, 0.5 or 0 mg per chamber, and *Shigella flexneri* 2a-5503 was inoculated at a density of $1 \times 10^7$ cells per chamber and cultured under the condition of fully humidified, 7.5% $CO_2$ in air at 37° C. for 2 hours, whereby Intestine-407 cells or Hela S-3 cells were infected with *Shigella flexneri*.

Subsequently, the culture medium was replaced by kanamycin-containing medium, and incubated for another two hours, after which the medium was removed, and cells were fixed with methanol and stained with Gimsa staining. The number of cells invaded by the said bacteria per about 1,000 cells was counted for each adding amount in three chambers, and from the average number, the percentage of invasion upon cells was calculated. As controls, glycogen and dextran were also subjected to the same test as described above. The results obtained were as shown in Table 1 and Table 2.

TABLE 1

Infection percentage (%) in Intestine-407 cells

| Adding amount (mg) | *Bifidobacterium infantis* polysaccharide (Example 1) | *Bifidobacterium longum* polysaccharide (Example 2) | Glycogen | Dextran |
|---|---|---|---|---|
| 0 | 100 | 100 | 100 | 100 |
| 0.5 | 81 | 77 | 97 | 87 |
| 1.0 | 52 | 59 | 92 | 81 |
| 1.5 | 40 | 43 | 80 | 76 |
| 2.0 | 26 | 32 | 69 | 74 |

TABLE 2

Infection percentage (%) in Hela S-3 cells

| Adding amount (mg) | *Bifidobacterium infantis* polysaccharide (Example 1) | *Bifidobacterium longum* polysaccharide (Example 2) | Glycogen | Dextran |
|---|---|---|---|---|
| 0 | 100 | 100 | 100 | 100 |
| 0.5 | 84 | 80 | 95 | 92 |
| 1.0 | 60 | 57 | 90 | 85 |
| 1.5 | 45 | 41 | 84 | 79 |
| 2.0 | 24 | 29 | 73 | 71 |

As is evident from Table 1 and Table 2, neither glycogen nor dextran exhibited a marked anti-infective activity on both cells, while the group subjected to addition of 1.5 mg of the polysaccharide was reduced in infection percentage to less than one-half those of the groups subjected to no addition: thus a marked anti-infective activity was exhibited. Therefore, the polysaccharide was found to have an anti-infective effect.

TEST 2

Anti-infective Test in Vivo

It has already been known that a highly pathogenic strain of *Shigella flexneri* which is pathogenic to the naturally sensitive animals (human and monkey) is specifically pathogenic also to the eyes of guinea pig, and that the pathosis of the eyes is in common with that of the intestine of the naturally sensitive animals in many points. By utilizing this fact, the anti-infective effect of said polysaccharide was further tested with respect to infection in the eyelids of guinea pig.

The polysaccharide produced in the same manner as in Example 1 and glycogen as a control were individually dissolved in physiological saline and dropped into the eyes of each guinea pig in an amount of 0.5, 2.5 or 5.0 mg per eye. At the same time, *Shigella flexneri* 2a was suspended in physiological saline and dropped into the eyes of the guinea pig at a density of $10^9$ cells per eye. After the lapse of 48 hours, occurrence of conjunctivitis or keratitis in the eyelids of the guinea pig was observed. The number of guinea pigs in each group was five.

The results were as shown in Table 3. As is evident from Table 3, in the case of the glycogen-treated group, four of five guinea pigs were attacked by the disease even at a dose of 5.0 mg. On the other hand, in the case of the polysaccharide-treated groups, three of five guinea pigs were attacked by the disease at a dose of 0.5 mg, but substantially complete protection against infection was observed at a dose of 2.5 mg.

TABLE 3

Anti-infective activity in a test of infection of *Shigella flexneri* 2a into the eyes of guinea pig

| Administered substance | Dose per one eye of guinea pig (mg) | Number of guinea pigs | Number of guinea pigs attacked by conjunctivitis or keratitis | Infection percentage (%) |
| --- | --- | --- | --- | --- |
| Physiological saline | — | 5 | 5 | 100 |
| Polysaccharide of Example 1 | 0.5 | 5 | 3 | 60 |
| | 2.5 | 5 | 1 | 20 |
| | 5.0 | 5 | 0 | 0 |
| Glycogen | 0.5 | 5 | 5 | 100 |
| | 2.5 | 5 | 5 | 100 |
| | 5.0 | 5 | 4 | 80 |

From these results, it was found that infection in the naturally sensitive animals could be prevented by administration of at least 2.5 mg of the polysaccharide even when the infection was much more severe than usual infection in vivo.

Further, as described above, the pathosis of the eyes of guinea pig is in common with that of the intestine of the naturally sensitive animals in many points, and it can therefore be presumed that the anti-infective substance agent of this invention (has also active) for infection in human intestine.

TEST 3

Toxicity Test

As test animals, A/J male and female mice (7 weeks old, body weight 22±2 g) were used. The polysaccharide (produced in the same manner as in Example 1) dissolved in physiological saline was administered orally in a dose of 1, 5 or 10 g per kilogram of body weight for 10 consecutive days. Physiological saline was administered to control group for 10 consecutive days. Ten mice per group were observed for 30 days after the administration, and the number of mice which died was counted.

The test results were as shown in Table 4.

TABLE 4

Results of toxicity test on polysaccharide

| Administration | Dose (g/kg) | Sex | Number of test mice | Number of mice which died | Mortality (%) |
| --- | --- | --- | --- | --- | --- |
| Control | — | ♂ | 10 | 0 | 0 |
| | — | ♀ | 10 | 0 | 0 |
| Polysaccharide of Example 1 | 1 | ♂ | 10 | 0 | 0 |
| | 1 | ♀ | 10 | 0 | 0 |
| | 5 | ♂ | 10 | 0 | 0 |
| | 5 | ♀ | 10 | 0 | 0 |
| | 10 | ♂ | 10 | 0 | 0 |
| | 10 | ♀ | 10 | 0 | 0 |

As is evident from Table 4, no mouse died at any of the doses of the polysaccharide. This result indicates that the polysaccahride of this invention has a very low toxicity.

TEST 4

Eyelid Irritation Test

An eyelid irritation test according to Draize method was carried out. Into the conjunctival sac of one eye of each of 10 rabbits per group was dropped 0.1 ml of a solution prepared by dissolving each of the polysaccharides produced by the same manner as in Examples 1 and 2 in physiological saline in a concentration of 100 mg/ml. After 1, 4, 24, 48 and 72 hours and 4 and 7 days, pathologic observation of the eyelid was carried out for group subjected to washing of the eyelid 5 minutes after the dropping (5-minutes exposed group) and groups subjected to washing of the eyelid 24 hours after the dropping (24-hours exposed group).

The results obtained were as shown in Table 5. By observation for 1 to 7 days, ulcer and turbidity in the cornea and iris, or cengestion, edema, ulcer and recrosis in the conjunctiva was observed in neither the 5-minutes exposed groups nor the 24-hours exposed groups.

TABLE 5

| | 5-Minutes exposed group | 24-Hours exposed group |
| --- | --- | --- |
| Example 1 | No abnormality was observed by observation for 7 days | No abnormality was observed by observation for 7 days |
| Example 2 | No abnormality was observed by observation for 7 days | No abnormality was observed by observation for 7 days |

From the above test results, it was confirmed that the phylactic agent of this invention has neither toxicity nor side effects.

EXAMPLE 1

Bifidobacterium infantis (ATCC 15697) was subjected to stationary culture in 25 liters of SE medium having the composition shown hereinafter at 37° C. for 24 hours, followed by heat pasturization at 65° C. for 40 minutes, and cells were collected by centrifugation. The cells were suspended in distilled water, disrupted by ultrasonification at 20 KHz for 20 minutes, and centrifuged to precipitate and removed undisrupted cells, and the supernatant was centrifuged at 28,000× g for 1 hour to obtain a precipitate. The precipitate was suspended in a 10 mM potassium phosphate solution containing 5 mM $MgCl_2$ and dispersed by means of a glass homogenizer, after which the resulting dispersion was centrifuged to obtain a precipitate. This precipitate was washed five times by carrying out the same procedure as described above except for using distilled water, dialyzed against distilled water, and then freeze-dried. The freeze-dried product was suspended in 20 mM $CaCl_2$ - 50 mM Tris-HCl buffer (pH 7.2) (hereinafter abbreviated to "Tris") containing trypsin (1 mg/ml), DNase (50 μg/ml), RNase (150 μg/ml) and $MgCl_2$ (10 mM), and subjected to hydrolysis at 37° C. for 18 hours. The treated suspension was centrifuged at 20,000× g for 40 minutes to obtain a precipitate. The precipitate was suspended in Tris containing trypsin (0.5 mg/ml) and α-chymotrypsin (0.5 mg/ml), and subjected to hydrolysis at 37° C. for 18 hours. The resulting treated suspension was centrifuged at 20,000× g for 40 minutes, and the precipitate was suspended in 0.01N HCl containing pepsin (1 mg/ml) and subjected to hydrolysis at 37° C. for 18 hours. The resulting treated suspension was centrifuged at 20,000× g for 40 minutes, and the pepsin digested precipitate was dispersed into Tris containing pronase P (Trade name mfd by Kanenkagaku Co., Ltd.) in a proportion of 1 mg/ml, and subjected to hydrolysis at 37° C. for 18 hours. The resulting treated suspension was centrifuged at 20,000 g for 40 minutes to obtain a precipitate. The pronase P treatment was repeated twice to obtain a precipitate. This precipitate was washed by suspending in distilled water, followed by centrifugation at 20,000× g for 40 minutes, and the precipitate separated was sufficiently dialyzed against distilled water and then freeze-dried. The freeze-dried product was suspended in a 5% (by weight) aqueous trichloroacetic acid solution 200 times as much as the freeze-dried product, and treated at 37° C. for 18 hours, after which the suspension thus obtained was neutralyzed with 2N NaOH solution. The insoluble component were filtered off, and the filtrate was concentrated under reduced pressure to one-half of its original volume, after which ethanol was added so as to adjust the final concentration to 90%, to precipitate a polysaccharide. The precipitate was dialyzed against distilled water and freeze-dried to obtain about 800 mg of the polysaccharide in powder form. The yield was about 4%.

| Composition of SE medium (per liter) | |
|---|---|
| Casein hydrolyzate (molecular weight: about 1,000 or less) | 25 g |
| $KH_2PO_4$ | 5 g |
| $Na_2HPO_4$ (anhydrous) | 5 g |
| Sodium acetate (anhydrous) | 1 g |
| Sodium chloride | 1 g |
| Lactose | 25 g |
| L—cystein.hydrochloride (monohydrate) | 0.04 g |
| Sodium pyruvate | 0.1 g |
| Alanine | 10 mg |
| Asparagine | 10 mg |
| Glutamine | 10 mg |
| Tryptophan | 10 mg |
| Serine | 10 mg |
| Calcium pantothenate | 0.2 mg |
| Biotin | 0.1 mg |

EXAMPLE 2

In the same manner as in Example 1 except for using *Bifidobacterium longum* (ATCC 15707), about 950 mg of a polysaccharide was obtained. The yield was about 4%.

EFFECT OF THE INVENTION

Effects brought about this invention are as follows.
(1) An anti-infective substance having a very low toxicity can be obtained.
(2) An anti-infective substance having very slight side effects can be obtained.
(3) An anti-infective substance having a very excellent anti-infective activity can be obtained.

What is claimed is:
1. A substance having an anti-infective activity comprising a polysaccharide separated from the cell wall of bacteria belonging to genus Bifidobacterium, wherein the substance has the following physical and chemical properties:
  (a) molecular weight; 15,000 to 200,000 daltons as determined by gel filtration;
  (b) constituent saccharides; mainly composed of glucose and galactose at the molar ratio of 1:about 2.8; and
  (c) elementary analysis; 44.6% of carbon, 6.2% of hydrogen and 0.2% or less of nitrogen.
2. A substance having an anti-infective activity according to claim 1, wherein the bacteria belonging to genus Bifidobacterium is selected from the group consisting of Bifidobacterium infantis, *Bifidobacterium longum* and mixture thereof.
3. An anti-infective agent for intestinal infectious disease containing as active material an effective amount of the substance of claim 2.
4. A substance having an anti-infective activity according to claim 1, which is soluble in water and insoluble in organic solvents.
5. An anti-infective agent for intestinal infectious disease containing as active material an effective amount of the substance of claim 4,.
6. A substance having an anti-infective activity according to claim 1, which shows in infrared absorption spectrum characteristic absorptions at wave number($cm^{-1}$) of 3600–3200 (strong), 2950–2850 medium), 1640 (medium), and 1160–1000 (strong).
7. An anti-infective agent for intestinal infectious disease containing as active material an effective amount of the substance of claim 6.
8. A substance having an anti-infective activity according to claim 1, which produces a color characteristic of saccharides in the α-naphthol-sulfuric acid reaction, indole-sulfuric acid reaction anthrone-sulfuric acid reaction and phenol-sulfuric acid reaction and not produce a color characteristic of protein or peptide in the bieuret reaction and Lowry-Folin's reaction.
9. An anti-infective agent for intestinal infectious disease containing as active material an effective amount of the substance of claim 8.
10. A substance having an anti-infective activity according to claim 1, which is white in color, and tastless and oderless powder.
11. An anti-infective agent for intestinal infectious disease containing as active material an effective amount of the substance of claim 10.
12. An anti-infective agent for intestinal infectious disease containing as active material an effective amount of the substance of claim 1.

* * * * *